(12) United States Patent
Hurtado

(10) Patent No.: US 6,341,237 B1
(45) Date of Patent: Jan. 22, 2002

(54) DEVICE FOR ADMINISTRATING ELECTRO-MUSCLE STIMULATION AND METHOD OF USE

(76) Inventor: Arthur F. Hurtado, 7750 Big Rock Dr., Riverside, CA (US) 92509

(*) Notice: Subject to any disclaimer, the term of this patent is extended or adjusted under 35 U.S.C. 154(b) by 0 days.

(21) Appl. No.: 09/425,996

(22) Filed: Oct. 25, 1999

(51) Int. Cl.[7] ................................................ A61N 1/04
(52) U.S. Cl. ........................ 607/148; 607/115; 607/152
(58) Field of Search ................................. 607/115, 148, 607/149, 152, 72; 600/372, 382, 390, 393

(56) References Cited

U.S. PATENT DOCUMENTS

| | | | | |
|---|---|---|---|---|
| 3,025,857 A | * | 3/1962 | Browner | 607/148 |
| 4,381,012 A | * | 4/1983 | Russek | 607/152 |
| 4,522,211 A | * | 6/1985 | Bare et al. | 607/152 |
| 5,010,896 A | * | 4/1991 | Westbrook | 607/115 |
| 5,344,440 A | * | 9/1994 | Stephen | 607/139 |
| 5,766,236 A | * | 6/1998 | Detty et al. | 607/115 |

* cited by examiner

*Primary Examiner*—George R. Evanisko

(57) ABSTRACT

A device for administrating electro-muscle stimulation (EMS) includes a flexible covering having a plurality of spaced apart electrodes (22). In a preferred embodiment the flexible covering is shaped like a belt (24) and is designed to encircle and be connected around a portion of a patient's body (506). The belt is fabricated from an elastic material so that the electrodes are pressed against the skin of the patient to promote better electrical conduction. The electrodes are selectively positionable to different locations on the belt, so they may be placed directly over a selected muscle or muscle group. Each electrode has its own individual control (32) for adjusting the level of the electrical stimulation signal, so that (1) different muscles can receive different levels of stimulation, and (2) the level of stimulation may be changed during the course of treatment. A master adjustment control (504) is used to adjust the stimulation signal level applied to all the electrodes. In a preferred embodiment, the individual adjustment controls are located adjacent their respective electrodes on the belt. In accordance with another preferred embodiment of the invention, the flexible covering (423) is folded to form a pocket, and a sponge assembly (425) is removably inserted into the pocket. The sponge assembly has a plurality of replaceable sponges (429).

11 Claims, 13 Drawing Sheets

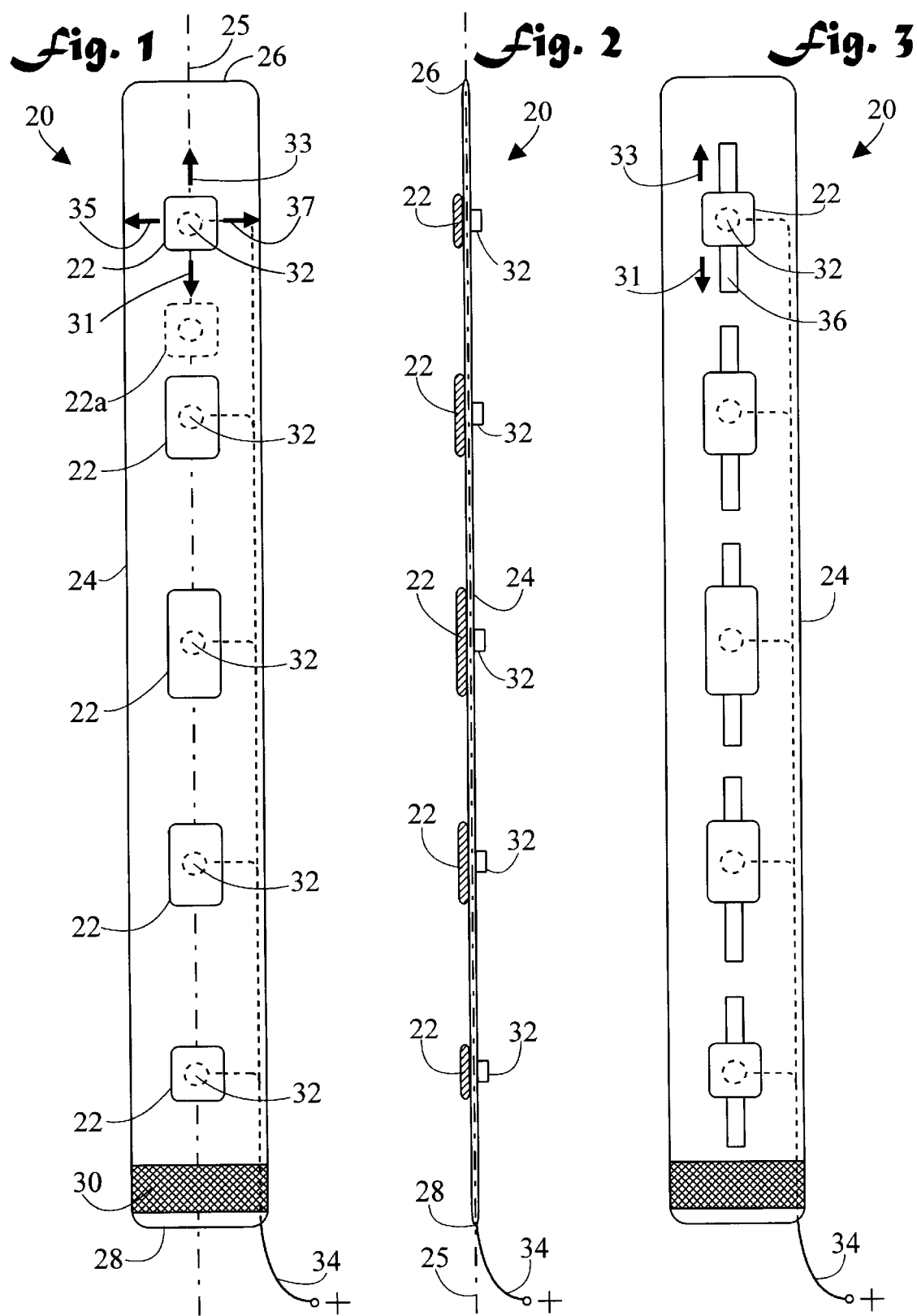

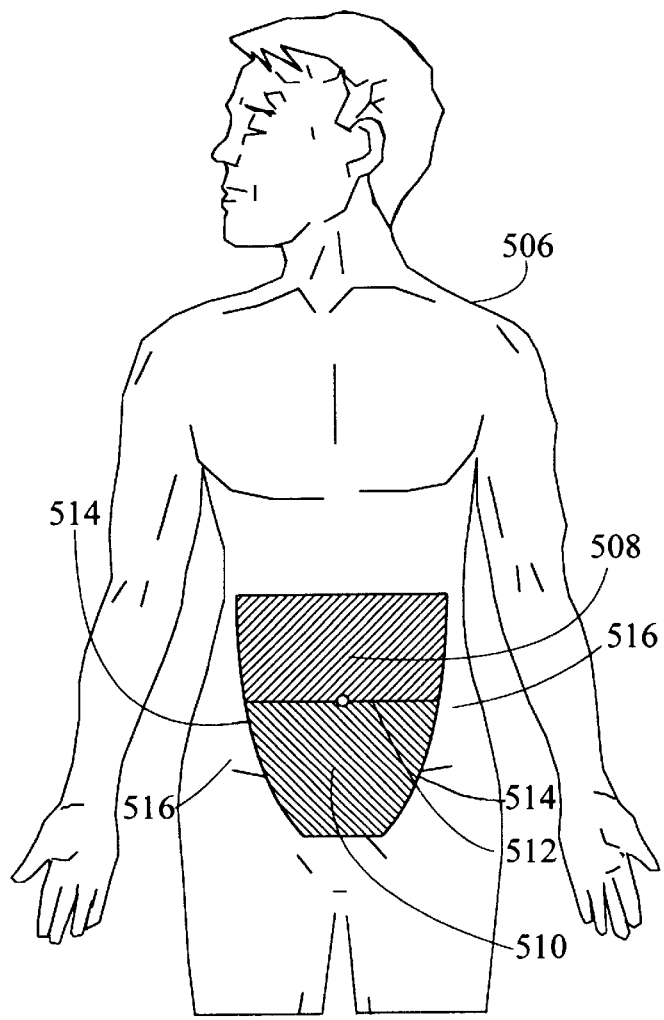
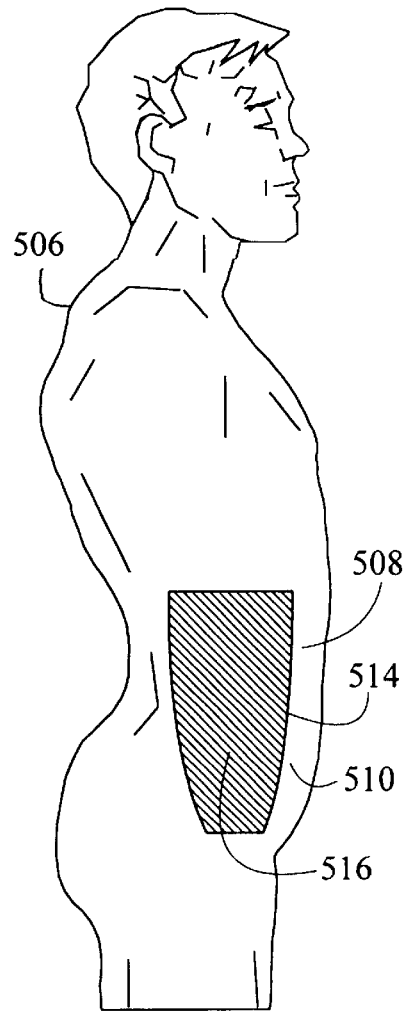

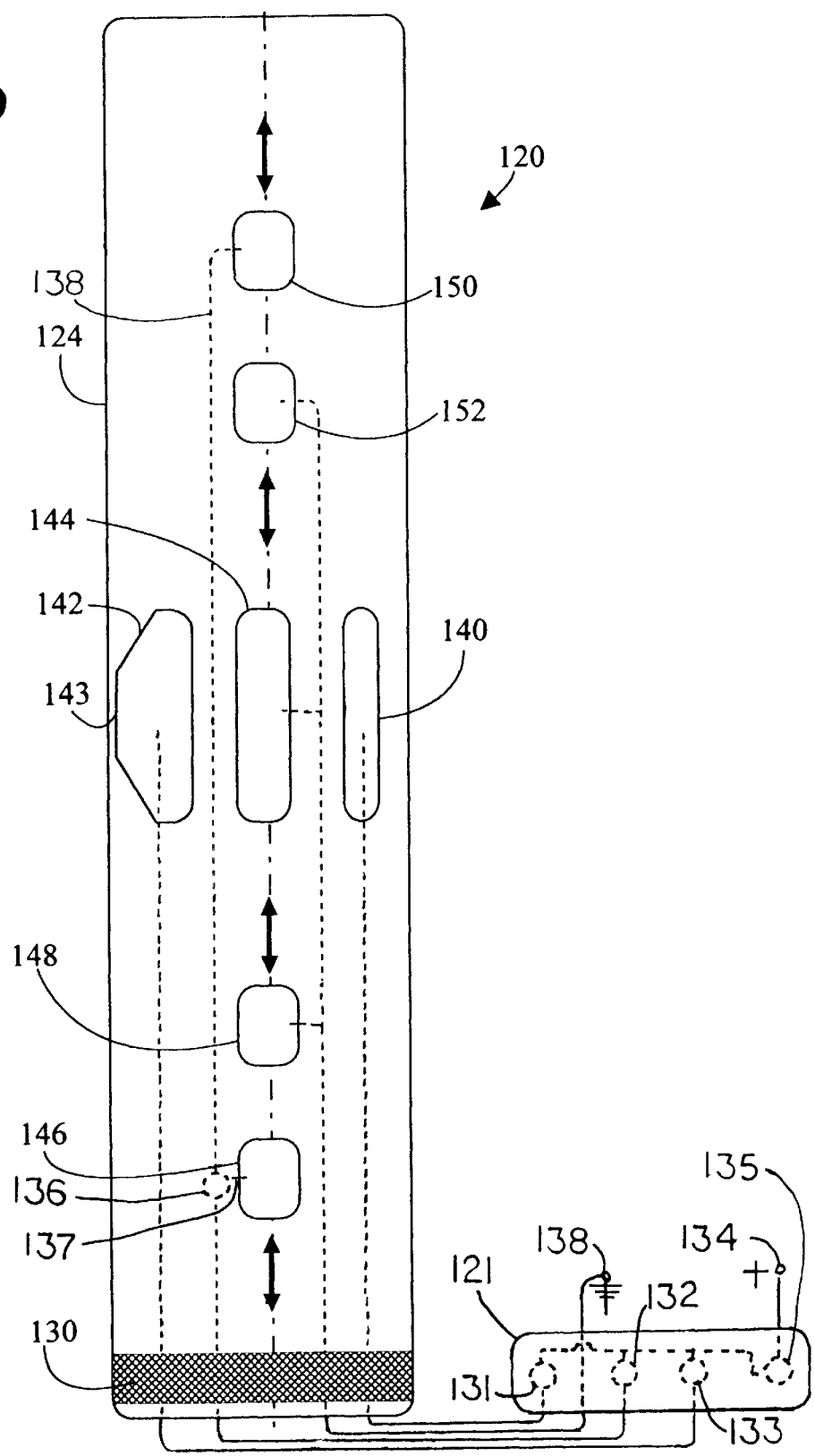

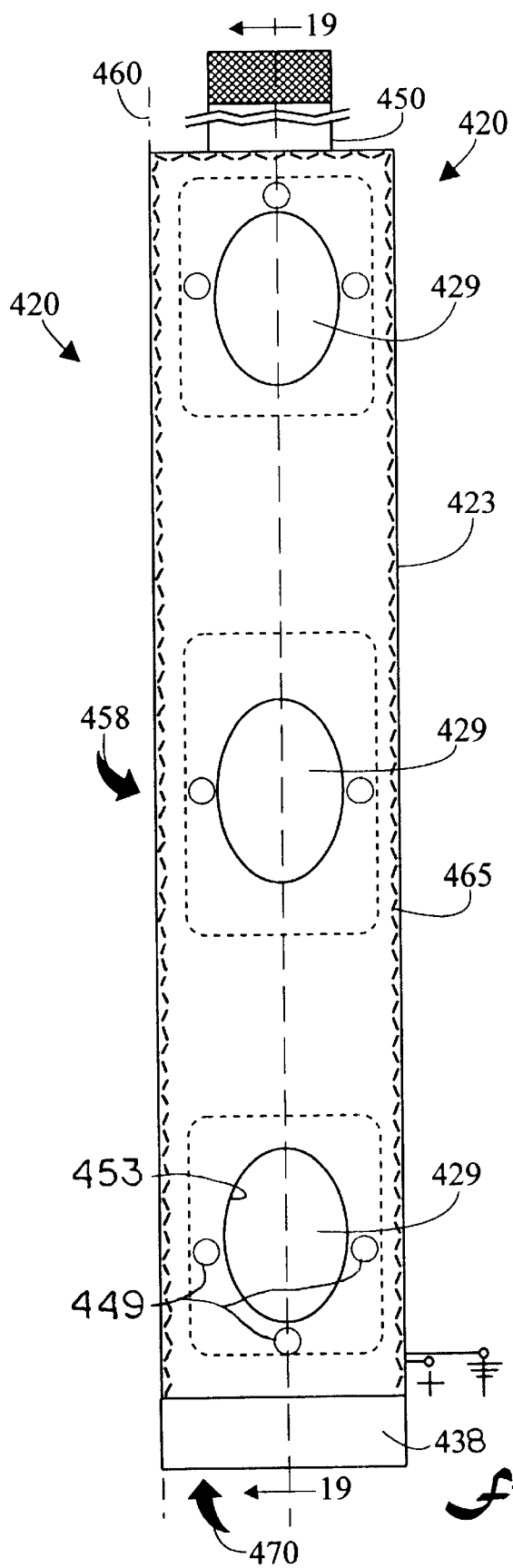
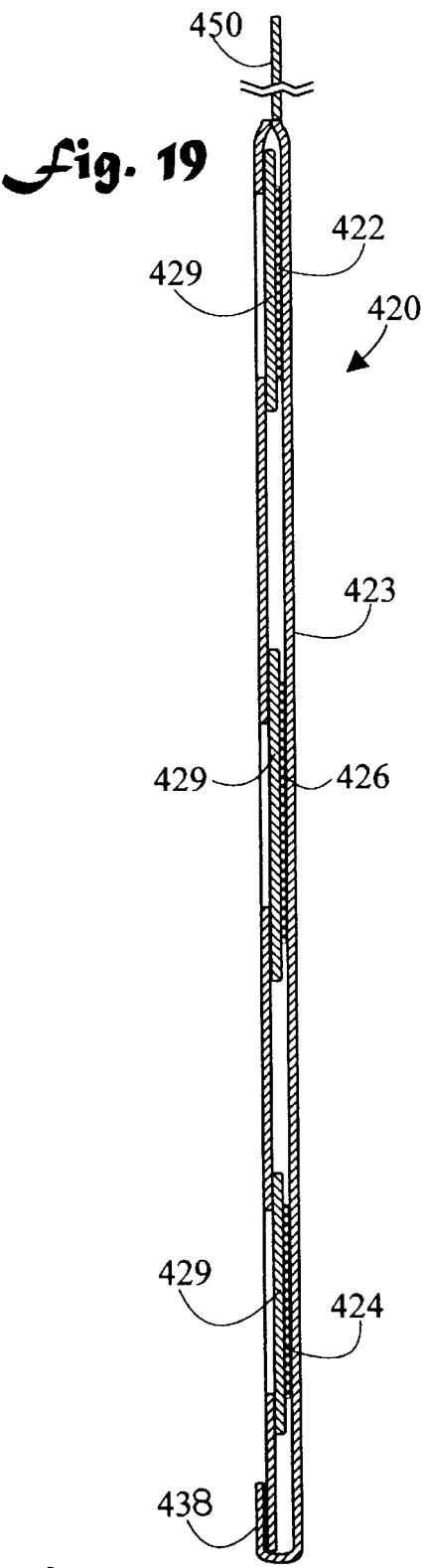
fig. 18
fig. 19

DEVICE FOR ADMINISTRATING ELECTRO-MUSCLE STIMULATION AND METHOD OF USE

TECHNICAL FIELD

The present invention relates generally to electro-muscle stimulation, and in particular to a belt-like device which is wrapped around or otherwise placed upon a portion of the body to administer adjustable levels of electrical stimulation.

BACKGROUND ART

Electro-muscle stimulation (EMS) is well known in the medical art. This technology utilizes a conductive pad or electrode to externally apply a very weak current to a muscle or group of muscles and thereby cause them to contract. The electrode receives an electric stimulation signal from an external voltage/current source, such as an EMS machine. The stimulation signal can be adjusted in amplitude, polarity, frequency, waveform, etc. EMS is commonly used in physical or occupational therapy to strengthen atrophied muscles or paralyzed limbs, and also to exercise muscles that are immobilized for long periods of time as a result of muscular or neurological disorders, extended periods of bed rest arising from injury, surgery, or illness. EMS is also useful for the general exercise of functional muscles to improve muscle tone and strength. For example with athletes, EMS can be used to treat muscle injuries as a supplement to conventional conditioning exercises. EMS can also be used to recondition muscles or muscle groups which have, for whatever reason, lost their tone and/or strength, have been injured, or are in need of reconditioning to effect cosmetic improvements. An operator who has been trained in the principles of EMS can analyze the areas which are of concern, and select the proper muscles to exercise and train.

For example, U.S. Pat. No. 4,480,830 illustrates a method and apparatus for exercising paralyzed muscles. The method and apparatus make use of a set of transcutaneous electrodes which are placed upon the skin of the subject over muscles which are to be stimulated. A computer controlled stimulator generates a pair of alternately pulsed stimulation signals which are applied across different pairs of stimulation electrodes to produce controlled muscle contraction. Muscle movement is resisted by a dynamic load and a position sensor provides a feedback signal indicating the movement actually achieved. The computer uses the feedback signal for modifying the control signal applied to the stimulator. U.S. Pat. No. 4,499,990 shows a system and method for treating persons with paralyzed legs. The apparatus and method include four sets of transcutaneous electrodes which are placed above the iliac and quadriceps muscles of the paralyzed person. The person is seated upon an exercycle and a series of pulsed stimulation signals are applied to the electrodes to cause coordinated contraction of the iliac and quadriceps muscles. This causes pedaling of the exercycle by the paralyzed legs. A position sensor senses the position of the pedals and transmits an indication thereof to a computer which generates control signals for stimulation driving circuits connected to the stimulation electrodes. U.S. Pat. No. 4,582,049 portrays a patient initiated response method for re-educating debilitated muscle tissue. The method comprises the detection of an electromyographic signal in a muscle group which is used to trigger an artificial stimulation signal of a higher predetermined intensity and transmit such a signal to a debilitated muscle group. The patient initiated electromyographic signal may be detected in a debilitated or non-debilitated muscle group. The operator determines the frequency and intensity of the stimulation signal. U.S. Pat. No. 4,586,495 illustrates an apparatus and method for stimulating muscular activity in an acutely injured patient. A leg which is to be stimulated is strapped into a brace and the leg muscles are stimulated to work isometrically against the brace. The effort exerted by the muscles is measured by load cells which generate feedback signals for a control computer. The computer adjusts the stimulation signals in accordance with the received feedback signals. U.S. Pat. No. 4,586,510 discloses an apparatus for exercising a paralyzed limb by functional electrical stimulation. The system utilizes simple analog devices including a reference signal generator, a position sensor, and an error signal generator. The error signal is integrated to produce a stimulation driving signal for application to the stimulation electrodes mounted on the limb. In the disclosed embodiment, the paralyzed person may be seated in an exercise chair which is equipped with a pair of loading assemblies which are attachable to the legs of the person so as to yieldingly resist the stimulated movement. U.S. Pat. No. 4,724,842 shows a method and apparatus for muscle stimulation. An exercise machine or dynamometer is provided with control apparatus for ascertaining the physical position of a patient during an exercise. The patient is then electrically stimulated over selected ranges of motion in order to aid in the exercise. U.S. Pat. No. 4,785,813 consists of an apparatus for assisting muscular contraction of a partially paralyzed muscle. The system uses a pair of electrode terminals which sense voluntary EMG signals at the site of the muscle and periodically transmit appropriately corresponding higher level stimulation signals. Stimulation signals are generated by a pulsed stimulator operating under control of an amplifier arrangement connected to receive the EMG signals from the electrode terminals. A transistor switch interrupts the amplifier output in synchronism with the generation of stimulation signals. U.S. Pat. No. 4,838,272 describes a method and apparatus for adaptive closed loop electrical stimulation of muscles. The method and apparatus strengthens skeletal muscles through maximizing muscle tension in which electrical stimulation signals are applied to the selected muscles at a predetermined frequency, pulse width, and amplitude, and work output by the muscles in response to stimulation signals is determined over a fixed period of time. The work output is compared to a defined value which can be a target value or a value measured during a previous stimulation period. U.S. Pat. No. 5,070,873 includes a method of and apparatus for electrically stimulating quadriceps muscles of an upper motor unit paraplegic. Muscle fatigue of an electrically stimulated quadriceps muscle of an upper motor neuron paraplegic is detected and compensated for by monitoring the myoelectric (EMG) signal produced by the stimulated muscle and controlling one or more of the following parameters of the electrical stimulation (ES) signal: pulse repetition rate, amplitude, and pulse width. U.S. Pat. No. 5,330,516 depicts a device for generating hand function having an S-type splint consisting of a forearm portion extending along the palmar side of the forearm, a palmo-dorsal transition portion leading to a dorsal portion extending across the dorsal side of the carpal bones of the hand, and a palmar portion which touches the palm of the hand of the wearer of the device at least indirectly. A plurality of electrodes are mounted on the splint in positions in which they can make contact with skin portions directly overlying the muscles to be stimulated. U.S. Pat. No. 5,507,788 illustrates a method and apparatus for controlling skeletal muscle fatigue during electrical stimulation. Electrical stimulation signals are applied to muscles at a frequency which is varied in response to a detected ripple signal in an output tension or torque record which corresponds to the fusion of the multiple muscle contractions. An average torque amplitude is first determined when a stimulation signal is applied at an initial frequency. The amplitude of the ripple on the torque output is then determined and compared to the average torque amplitude to provide a ripple percentage. The measured ripple percentage is compared to a selected ripple percentage corresponding to the desired fusion of the multiple muscle contractions. And the stimulation frequency is adjusted by a feedback loop until the measured ripple percentage conforms to the selected value. U.S. Pat. No. 5,628,722 shows a method for maintaining knee stability of a user suffering from damage to a knee ligament. The method includes a sensor feedback system for measuring abnormal physical relationships between the tibia and femur. The sensor feedback system determines whether selected conditions have been met warranting the application of electrical stimulation and provides information regarding the determination to an electronic stimulator. Electrodes are spaceably mounted on the hamstring and/or quadriceps muscles in electrical communication with the electronic stimulator for causing contraction of the thigh muscles at selected levels, thus providing a posteriorly and/or anteriorly directed force to the upper tibial bone and thereby preventing its instability.

DISCLOSURE OF INVENTION

The present invention is directed to a device for administrating electro-muscle stimulation (EMS) which comprises a flexible covering containing positionable electrodes which are strategically placed upon a patient's body to stimulate specific muscles or muscle groups. In a preferred embodiment, the covering is in the form of a belt or band which is snugly wrapped around a portion of the patient's body. The belt is typically used in conjunction with an EMS machine which emits an electrical voltage/current for activating the electrodes. The electrodes in turn cause the selected muscles to contract. By placing the electrodes in specific locations within the belt, and correlating these sites over targeted muscles, contraction of the desired muscles is made possible. The present invention also provides means for stimulating muscles that are otherwise difficult to exert, and furthermore causes muscles to contract further than would be the case with normal exercise or usual muscle contraction. The present invention may be used to augment and enhance natural exercise to encourage maximum muscle contraction, and can significantly extend the duration of an exercise period. Controls are provided allowing a user to establish the level of stimulation, and to adjust or "tune" the level of stimulation applied to specific muscle or muscle group sites.

In one preferred embodiment, the present invention comprises an "extremity cuff" which is useful in stimulating muscles in the legs and arms. The electrodes are placed in a line along the length of the cuff, and may be longitudinally positioned to accommodate the stimulation of specific muscles. Also in a preferred embodiment, two cuffs are simultaneously utilized, with one cuff containing positive electrodes and the other cuff containing the negative or return electrodes. It is noted that both positive and negative (return or common) electrodes are required in order to develop a stimulation current flow. Each electrode has a stimulation level control. In this manner, each electrode can be individually adjusted, and is thereby capable of varying the stimulation intensity at a targeted muscle or muscle group.

For the purpose of easy handling, the two cuffs may be abutted together with the use of a hook and loop attachment means such as sold under the trademark Velcro®, and thereby serve as one intact unit. Alternatively, the positive and negative cuffs may be separated from each other along the length of a muscle, such as at the opposite ends of a thigh. For more versatility, each cuff may be rotated around the extremity for fine adjustment. The cuff also has a Velcro synching belt so that pressure is applied to force the electrodes into close contact with the skin of the patient, thereby enhancing the conduction of the stimulation signal. The electrodes and cuff are composed of a pliable material, so that they conform around the circumference of the arm or leg being stimulated. Also, the cuff may be made of an elastic material to allow stretching. By stretching the cuff, the electrodes may be relocated or selectively positioned to ensure proper placement with respect to the site being stimulated. Or electrodes within the cuff may be relocated or selectively positioned. In addition, the elastic material provides flexibility so the muscles can contract and relax without displacing the electrodes.

Extra electrodes on each end of the cuff provide the capability of adjusting the length span of the electrical stimuli. This is useful in that the length of the cuff, active with electrical stimuli, may be adjusted to fit different extremity circumferences. Electrodes on each end of the cuff may be turned off or on, allowing the cuff to adjust for different sizes of extremity girth.

A unique feature of the cuff having multiple adjustable electrodes is that the user may stimulate specific portions of a muscle group differently from other portions. This becomes especially useful in correcting muscular imbalances as seen in patients after muscular injuries, surgeries, strokes, or biomechanical dysfunctions. For instance, a muscle group such as the quadriceps often does not become uniformly deficient. Either the medial portion or the lateral portion will become more deficient over the other. Therefore, it is imperative that certain sections be developed over others to restore normal function. As an example, a deranged patella (kneecap) that is laterally displaced does not properly track over the femoral surface or groove. As the knee is extended and flexed, the patella improperly rides over the lateral crest of the femoral groove creating pain. Ultimately degenerative changes occur. In these instances, it is necessary to develop the medial portion of the quadriceps over the lateral to correct the problem. This development may be accomplished with the use of the present invention.

In another preferred embodiment, the present invention comprises an abdominal belt with three specific channels which are strategically bilaterally placed to contact the lower portions of the abdominus rectus, the upper portions of the abdominus rectus, and the obliques on both sides. A master control determines the overall stimulation intensity of all electrodes, and separate individual controls determine the stimulation intensity of each electrode. The most significant advantage of the separate controls is to allow the user to decide where to place the most emphasis. For example, by delivering higher voltage to the lower portions of the rectus abdominus and the obliques, they may be stimulated more than the upper portions of the rectus abdominal which are easier to exercise. The belt is made of an elastic pliable material to allow mobility of the body of the user. This provides the option for a person to exercise concurrent with the electrical surge.

The abdominal belt has one positive electrode located over the upper portions of the rectus abdominus, one positive electrode located over the lower portions of the rectus abdominus, and a negative or return electrode located in the umbilical region. By sharing one common electrode, elimination of one negative or return electrode is made possible. When the upper rectus abdominus electrode is solely activated, muscle contraction occurs between the upper portions of the abdominus rectus and the umbilical region. Conversely, when the lower rectus abdominus electrode is solely activated, muscle contraction occurs between the lower portions of the abdominus rectus and the umbilical region. When the upper and lower rectus abdominus electrodes are simultaneously activated, the electrode at the umbilical region serves as the negative or return electrode for both the upper and lower rectus abdominus electrodes. Consequently, there tends to be a higher electrical stimulation intensity at this region. However, this is a favorable phenomena since the umbilical region tends to have a thicker layer of fatty tissue. A higher level of stimulation intensity is required to penetrate the layer of fat in order to stimulate the underlying muscle wall. Additionally, higher levels of stimuli cause stronger muscular contractions and greater toning results.

Although the upper and lower portion of the abdominals comprise predominately the same muscle, rectus abdominus, it is important to separate them into two portions with respective and distinctive electrical stimulus controls. The upper portions of the rectus abdominus require less electrical stimulus because of their increased sensitivity due to decreased thickness and proximity to the underlying sternum and ribs. Additionally, the upper portions of the rectus abdominus are easier to exert with normal exercise than the lower portions of the rectus abdominus, thereby usually requiring less emphasis.

The shape of the electrode for the lower portions of the rectus abdominus is in the form of an truncated "V", with the apex toward the pubes. This configuration avoids stimulation of the femoral nerve at the inquinal area, and the undesired sensation along the femoral nerve into the leg. Alternatively, an insulative pad may be placed over the inguinal area to avoid stimulation of the femoral nerve.

Each group of oblique muscles, right and left, has its own set of positive and negative electrodes. The placement of these electrodes is adjustable to accommodate differences in anatomical make up and waist size. The negative electrode is placed toward the midline adjacent the negative electrode for the rectus abdominus in the umbilical region to minimize interference between the operation of the electrodes for the different muscles. Since current will take the shortest route between opposing poles or electrodes, the electrical stimulation intensity of each oblique is isolated from the other and will not affect the electrical stimulation intensity to the rectus abdominus. Similarly, the electrical stimulation intensity to the rectus abdominus will not affect the obliques. Proper placement of opposing electrodes is important. It enables controlling the pathway of electrical stimulus, either promoting stimulus along the bodies of specific muscles, or avoiding stimulus over undesired areas, such as the femoral nerve and ovaries.

Additionally, the negative electrodes of the obliques are placed at the junction of the rectus abdominus and external obliques. This area is especially rich with motor points. Motor points are areas that are reactive to stimuli, requiring less electrical intensity. Further, development of this area has the aesthetic property of enhancing definition making the differential between the abdominus rectus and the obliques more pronounced.

It is biomedically important to stimulate the right and left oblique muscles equally to achieve equal muscular development. Imbalances in muscular development may lead to musculoskeletal problems. Since the obliques are on opposite sides of the abdomen, each side requires its own set of electrodes which makes it more difficult to achieve equal stimulation. Numerous factors make equal stimulation difficult. The placement of the electrodes over the muscle with respect to the right and left side is important. One side may be more favorably placed over motor points or muscle fibers than the other, causing a stronger contraction. Conduction between the electrodes and the skin is another factor which determines the strength of muscular contractions. Conduction properties are influenced by the amount of moisture or conducting gel on the electrodes and the amount of pressure forcing the electrode against the skin. All of these factors make it necessary to incorporate a balance adjustment component to divert electrical stimulus to one side or the other in order to obtain equally balanced muscular contraction of the left and right obliques. In contrast, the left and right rectus abdominus are butted so close to each other that they are much more likely to contract equally and may share the same electrodes. A balance control at this site is therefore not necessary.

Typically abdominal exercises are divided into three areas of concentration: the upper portions of the rectus abdominus, the lower portion of the rectus abdominus, and the right and left obliques. For each of these areas specific exercises are performed to put special emphasis on the area. For example, stomach crunches with knee bends are used for the upper portions of the rectus abdominus, hip thrusts or straight leg crunches are used for the lower portions of the rectus abdominus, and oblique crunches or side crunches are used for the obliques.

In actuality, it is impossible to solely separate muscular action of any of these groups from each other. They all contract simultaneously to some extent when any one is stimulated. The exercises cited above merely apply heavier emphasis on one area over the others. However, applying emphasis to specific areas is required to achieve favorable results in the long run. For example, it is more difficult to exercise the obliques and lower portions of the rectus abdominus that it is to exercise the upper portion of the rectus abdominus. Consequently, the obliques and lower portions of the rectus abdominus are often neglected and become problem areas. The present invention enables direct emphasis on any of the aforementioned areas, or any combination of intensities to any of the areas as desired. This allows versatility in the targeting of problem areas without the necessity for specific exercises for the problem areas.

The versatility of the present invention lends itself to the fact that everyone has different builds and different needs. For example, women after child birth lose tonicity in the lower portions of the rectus abdominus and develop a pelvic pouch. Obviously, in this case it is more desirable to emphasize the lower portions of the rectus abdominus. Men tend to develop love handles. More emphasis should then be placed on the oblique muscles. In each of these cases, the specific exercises for these problem areas can be extremely difficult to perform and people often just lose hope and do nothing. The present invention allows them to exercise these areas easily.

The embodiments of the present invention may obtain their electrical power from a conventional electrical muscle stimulation (EMS) machine used in physical therapy applications, or may be powered by a portable battery type unit.

The belt may be used either passively or actively. In the passive capacity, the user exerts no activity and the electrodes artificially stimulate the muscles. In this passive state, the EMS machine controls all muscular contractions by automatically emitting electrical surges. The surges may be adjusted to suit the needs of the user. The EMS machine has controls that adjust the amplitude of the surge, the duration of the surge, and the rest period between each surge. The belt may also be used in an active capacity in which it is used to augment exercise. In this aspect the belt directs and targets muscle groups as determined by the user while simultaneously exercising. For example, the output of the EMS machine may be adjusted automatically by a potentiometer attached and moved by the exercise equipment utilized by the person.

Another advantage of the present invention is that it is cost effective. Typically, when numerous electrodes are placed at different sites on the body, more sophisticated EMS machines are used. In order to control the intensity of each electrode, the EMS machine requires a separate outlet channel for each set of electrodes. The cost of an EMS machine drastically increases with an increase in the number of output channels due to the increased circuitry required to produce each stimulation signal. Conversely, the present invention splits the electrical current and only one outlet channel is required in the EMS machine. The electrical components are far less extensive in the present invention, thereby resulting in a more cost effective device.

In accordance with a preferred embodiment of the invention, a device for administrating electro-muscle stimulation (EMS) includes a flexible covering having a plurality of spaced apart electrodes. In a preferred embodiment the flexible covering is shaped like a band or belt, and is designed to encircle and be snugly connected around a portion of a patient's body.

In accordance with an important aspect of the invention, the band or belt is fabricated from an elastic material so that the electrodes are pressed against the skin of the patient allowing the locations of the electrodes to be adjusted.

In accordance with an important feature of the invention, the band or belt is made in a plurality of sizes to fit different size persons and different portions of the body.

In accordance with another important aspect of the invention, the electrodes are selectively positionable to different locations on the flexible covering or band, so that they may be placed directly over a selected muscle or muscle group.

In accordance with another important feature of the invention, each electrode has its individual control for adjusting the level of the electrical stimulation signal, so (1) that different muscles can receive different levels of stimulation, and (2) the level of stimulation may be changed during the course of treatment.

In accordance with another important aspect of the invention, a master adjustment control is used to adjust the stimulation signal level applied to all electrodes.

In accordance with another important feature of the invention, the individual adjustment controls are located adjacent their respective electrodes on the flexible covering or band.

In accordance with an important aspect of the invention, the electrodes are placed in a pattern which matches predetermined groups of muscles, the muscles being the upper portions of the rectus abdominus, the lower portions of the rectus abdominus, and the obliques.

In accordance with an important feature of the invention, the electrodes receive either a positive or negative stimulation signal, and are positioned upon the flexible covering or band so that stimulation interaction between different muscle groups is minimized.

In accordance with an aspect of the invention, the electrode which stimulates the lower rectus abdominus, is shaped so as to avoid stimulation of the femoral nerve.

In accordance with another preferred embodiment, a return electrode is positioned between two positive electrodes. The voltage to the two positive electrodes is controllable so that as the voltage to one is increased, the voltage to the other is decreased, and visa versa.

In accordance with another preferred embodiment of the invention, the flexible covering is folded to form a pocket, and a sponge assembly is removably inserted into the pocket. The sponge assembly contains a plurality of removable sponges.

Other features and advantages of the present invention will become apparent from the following detailed description, taken in conjunction with the accompanying drawings, which illustrate, by way of example, the principles of the invention.

BRIEF DESCRIPTION OF DRAWINGS

FIG. 1 is a top plan view of an extremity cuff for administrating electro-muscular stimulation in accordance with the present invention;

FIG. 2 is side elevation view of the device;

FIG. 3 is a top plan view of a second extremity cuff embodiment having positionable electrodes on tracks;

FIG. 7 is a front elevation view of a patient;

FIG. 8 is a side elevation view of the patient;

FIG. 9 is a top plan view of an abdominal embodiment of the present invention;

FIG. 18 is a top plan view of the fifth extremity cuff embodiment in the folded and ready for use configuration;

FIG. 19 is a cross sectional view along the line 19—19 of FIG. 18;

MODES FOR CARRYING OUT THE INVENTION

Figure 4:
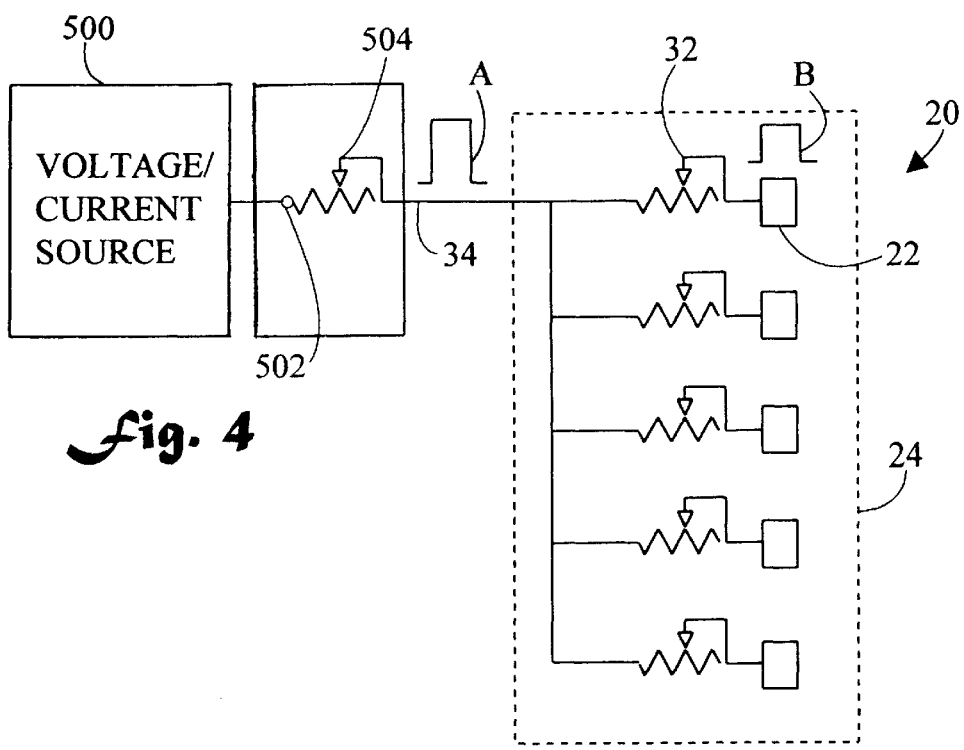
FIG. 4 is a first schematic diagram.

Referring initially to FIGS. 1 and 2, there are illustrated top plan and side elevation views respectively of an extremity cuff device for administrating electro-muscular stimulation (EMS) in accordance with the present invention, generally designated as 20. Device 20 includes a flexible covering having a plurality of spaced apart EMS electrodes 22, five in the shown extremity cuff embodiment. Electrodes 22 can be of various types and are well known in the art. In a preferred embodiment, the flexible covering has the general shape of a band 24 or belt having a longitudinal axis 25, two opposite ends 26 and 28, and a connector 30 disposed near one end for connecting the two ends 26 and 28 together. In a preferred embodiment, connector 30 includes hook and loop type fasteners, wherein band 24 is fabricated from one of hooks and loops, and connector 30 is fabricated from the other of hooks and loops, so that band 24 may be fastened around an extremity such as an arm or leg at any desired diameter. Also, in a preferred embodiment, band 24 is fabricated from an elastic material so that once it is wrapped around an arm or a leg, it resiliently grasps the extremity and provides versatility for placement of the electrodes on desired muscles. It may be appreciated that the flexible covering could also be of a form which does not completely encircle an extremity, but rather simply is placed upon and abuts an area of treatment.

Electrodes 22 are selectively positionable to different locations on the flexible covering so as to permit placement directly over desired muscles or muscle groups. In FIG. 1, top electrode 22 has been selectively moved downward in direction 31 to position 22a. Movement upward in direction 33, and/or sideways in directions 35 and 37 is also possible. One way to effect the selective placement is for electrode 22 to have a backing of hook material which cooperates with the loop material disposed upon the flexible covering. A wire tether connects electrode 22 to individual adjustment control 32 (see below), so that electrode 22 can be moved. Flexible covering or band 24 also can be fabricated in a plurality of different sizes to accommodate different size individuals, such as children and grownups.

Each electrode 22 has an individual adjustment control 32. In a preferred embodiment, individual adjustment control 32 is proximate to its corresponding electrode 22, and in one preferred embodiment is disposed upon the flexible covering or band 24 directly adjacent to electrode 22. Each electrode 22 is connected, via its individual adjustment control 32, to a stimulation signal 34 provided by an EMS machine or other signal source.

Electrodes 22 are adjustably disposed in a pattern which matches a predetermined group of human muscles, so that when flexible covering or band 24 is placed upon a patient, the electrodes 22 are proximate to the predetermined group of muscles.

FIG. 3 is a top plan view of a second extremity cuff embodiment having positionable electrodes 22 on tracks. Stimulation signal 34 is electrically connected to a plurality of conductive tracks 36, one track 36 for each electrode 22. Each electrode 22 and its associated adjustment control 32 may then be selectively positioned downward in direction 31 or upward in direction 33 along track 36.

FIG. 4 is a first schematic diagram. A voltage source 500, such as an EMS machine, provides an electrical stimulation signal. The practitioner adjusts a control on the EMS machine to a maximum desired voltage. This output provides an electrical stimulation signal input 502 to a master adjustment control 504 that the patient controls, then to each individual adjustment control 32, and then to each electrode 22. The stimulation signal input 502 can be in the form of an AC signal, a DC signal, a pulsed signal, etc. The master adjustment control 504 and individual adjustment controls 32 comprise potentiometers which selectively adjust the level of stimulation signal delivered to the electrode 22. For example, the electrical stimulation signal provided by the EMS machine is about 3 volts. Using the master adjustment control 504, the 3 volts can be lowered to a desired lesser value A, such as a mid-range value of 1.5 volts, for delivery to all electrodes 22 via the corresponding individual adjustment controls 32. The individual adjustment controls 32 can then be used to further lower the output of the master adjustment control 504 to a value of B. As was previously disclosed, the individual adjustment controls 32 are preferably located on the flexible covering (band 24) directly adjacent (above) the corresponding electrode 22.

Figure 5:
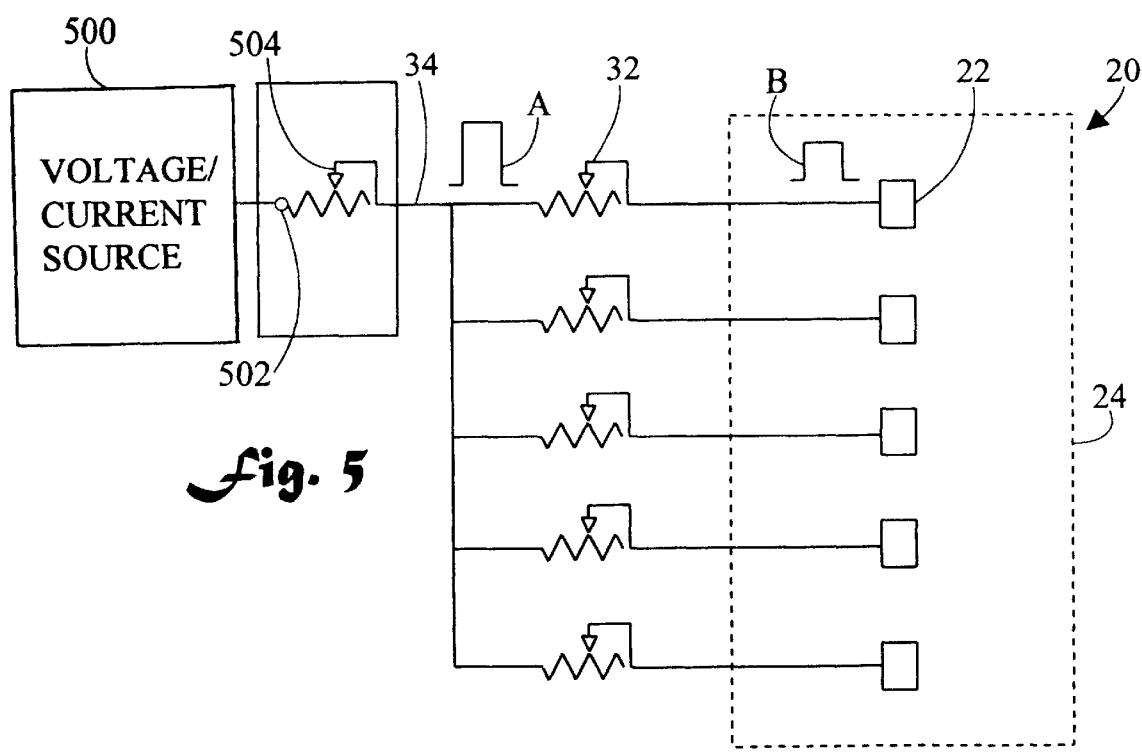
FIG. 5 is a second schematic diagram.

FIG. 5 is a second schematic diagram. This configuration differs from FIG. 4 only in that individual adjustment controls 32 are not located on the flexible covering (band 24), but are rather remotely located.

Figure 6:
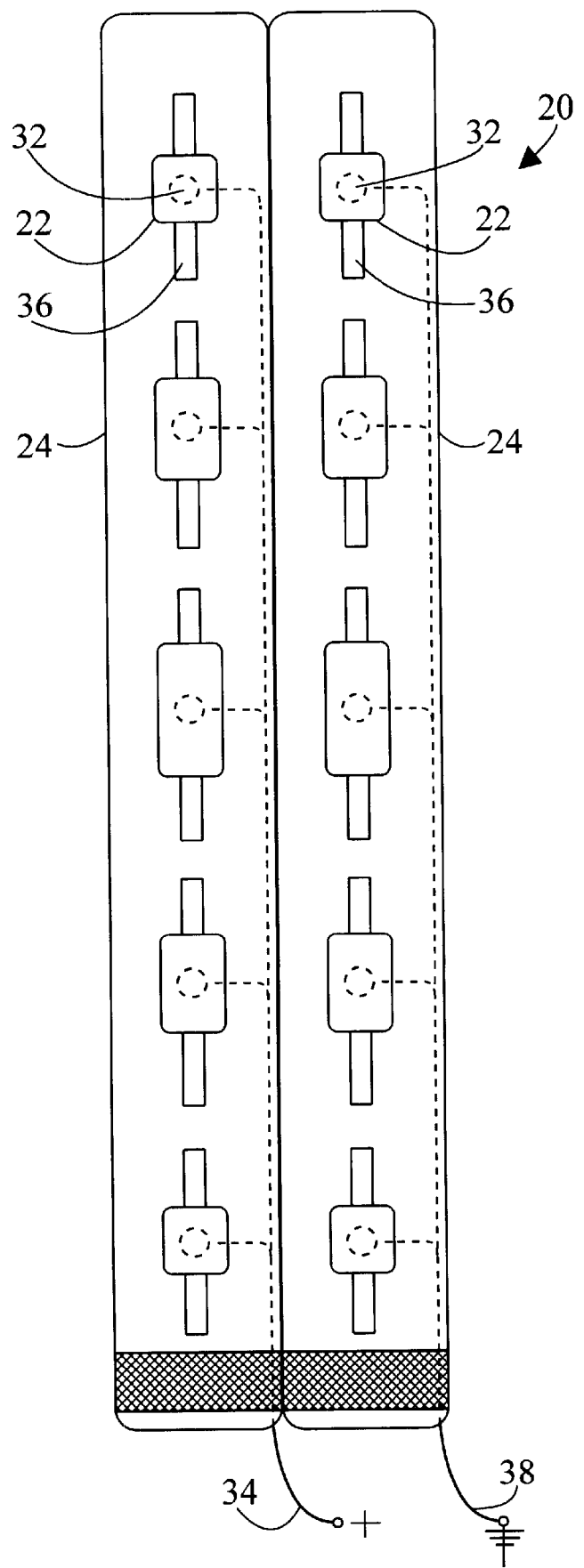
FIG. 6 is a top plan view of two devices traversely joined together.

FIG. 6 is a top plan view of two extremity cuff devices 20 of the second embodiment shown in FIG. 3 traversely joined together. One device 20 receives a positive stimulation signal 34, and the other receives a negative (return or common) stimulation signal 38. The cooperating positive and negative signals are required in order to promote a current flow between electrodes 22 of the two devices 20.

FIG. 7 is a front elevation view of a patient 506 showing the muscles of the rectus abdominus divided at the umbilical area 512 into an upper portion 508 and a lower portion 510. The rectus abdominus includes two distinct muscles on opposite sides of the linea alba. But for purposes of this invention, they work together and are stimulated together. Line 514 defines the junction of the right and left obliques 516 with the upper portion 508 and lower portion 510 of the rectus abdominus (refer also to FIG. 8).

FIG. 8 is a side elevation view of the patient 506 showing the right obliques 516. The left obliques are on the opposite side. Line 514 defines the junction of the right obliques 516 with the upper portion 508 and lower portion 510 of the rectus abdominus.

FIG. 9 illustrates a top plan view of the outside of an abdominal embodiment of the device of the present invention, generally designated as 120. The abdominal embodiment is specifically designed to encircle the abdomen and stimulate the muscle groups of the central torso. Abdominal embodiment 120 is similar in construction to extremity cuff embodiment 20 and includes a flexible covering or band 124, selectively positionable electrodes 146, 148, 150, and 152, and connector 130. Some of the electrodes receive a positive stimulation signal 134 and some receive a negative stimulation signal 138. The stimulated muscles (FIGS. 7 and 8) are the upper portion 508 and the lower portion 510 of the rectus abdominus, the right obliques 516, and the left obliques. Abdominal embodiment 120 includes a first positive electrode 140 which, when placed upon a patient, is proximate to the upper portion 508 of the rectus abdominus, a second positive electrode 142 which, when placed upon a patient, is proximate to the lower portion of the abdominus rectus, and a third negative return or common electrode 144 disposed between first 140 and second 142 positive electrodes in the umbilical region 512. Return electrode 144 provides a conduction path for both first positive electrode 140 and second positive electrode 142. It is noted that second positive electrode 142 has a truncated shape, in the form of edge 143, so as to avoid stimulation of the femoral nerve.

A fourth positive electrode 146 is placed on the left obliques on the side of the abdomen above the iliac crest and a fifth return electrode 148 is placed proximate to the junction 514 of the left obliques 516 and the upper and lower portions 508 and 510 of the rectus abdominus. The fifth return electrode 148 is disposed between the fourth positive electrode 146 and third return electrode 144. By placing the return electrodes 144 and 148 adjacent to each other, the electrodes which stimulate the abdominus rectus are electrically isolated from the electrodes which stimulate the obliques thereby minimizing stimulation interaction. A sixth positive electrode 150 is placed on the right obliques on the side of the abdomen above the iliac crest and a seventh return electrode 152 is placed proximate to the junction 514 of the right obliques 516 and the upper and lower portions 508 and 510 of the rectus abdominus. The seventh return electrode 152 is disposed between the sixth positive electrode 150 and third return electrode 144 in order to again minimize stimulation interaction.

A voltage source such as an EMS machine provides the signals 134 and 138. An overall control box 121 can be attached to the device 120, located nearby, or attached to an exercise device such as an ab roller exerciser. Individual adjustment controls 131, 132, and 133 determine the voltage delivered to first positive electrode 140, fourth and sixth positive electrodes 146 and 150, and second positive electrode 142, respectively. A master adjustment control 135 provides overall voltage control to the individual controls 131, 132, and 133. An adjustment control 136 simultaneously applies a first positive voltage 137 to fourth positive electrode 146 and a second positive voltage 138 to sixth positive electrode 150. As first positive voltage 137 increases, second positive voltage 138 decreases. And as first positive voltage 137 decreases, second positive voltage 138 increases.

Figure 10:
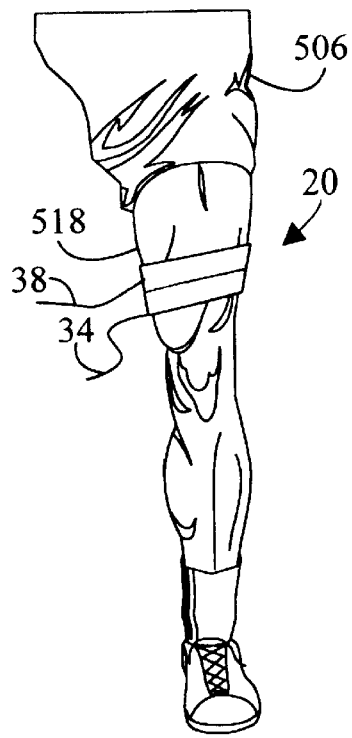
FIG. 10 is a front elevation view of two of the extremity cuff embodiments installed on the leg of a patient.

FIG. 10 is a front elevation view of two of the extremity cuff embodiments 20 of the present invention as shown in FIG. 6 installed on the leg 518 of a patient 506. Devices 20 have been wrapped around and encircle leg 518. In the shown embodiment at least one of the electrodes 22 is connected to a return signal 38 while others are connected to a positive stimulation signal 34. In this manner, a path for electrical current is provided.

Figure 11:
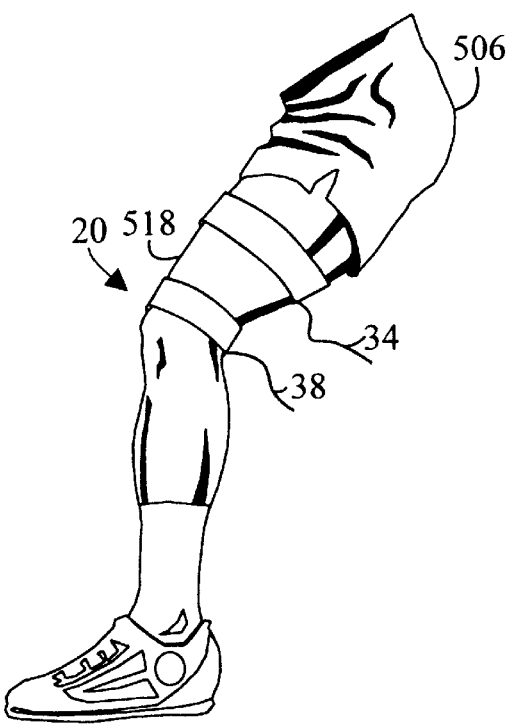
FIG. 11 is a side elevation view of two spaced extremity cuff embodiments installed on the leg of a patient.

FIG. 11 is a side elevation view of two spaced extremity cuff embodiments 20 installed on the leg 518 of a patient 506. One device 20 is connected to a positive stimulation signal 34, and the other device 20 is connected to a negative or return stimulation signal 38.

Figure 12:
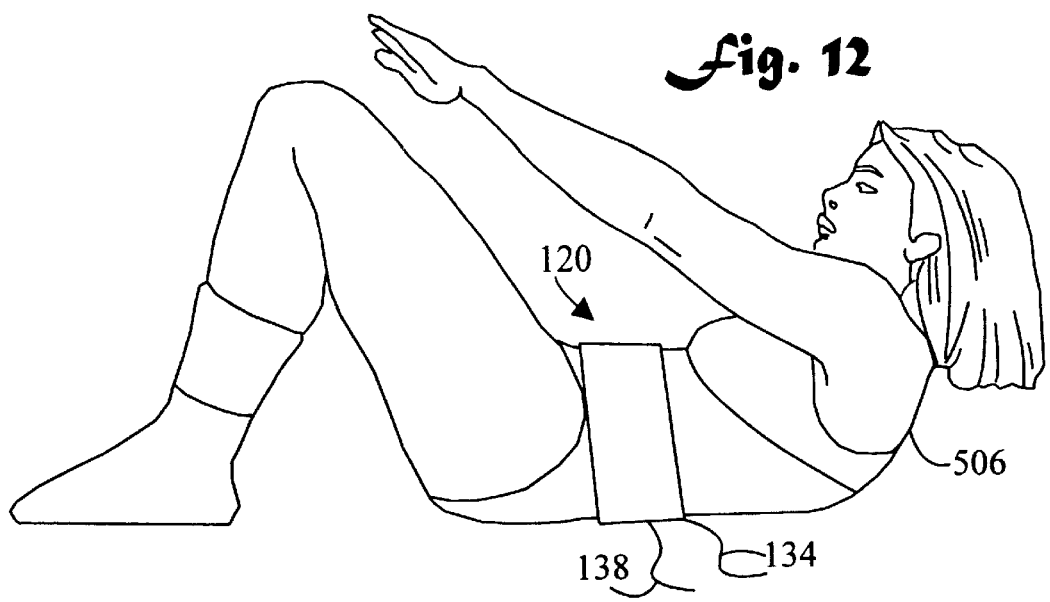
FIG. 12 is a side elevation view of the abdominal embodiment installed on an exercising patient.

FIG. 12 is a side elevation view of the abdominal embodiment 120 installed on an exercising patient 506. Device 120 stimulates the muscles as was described under the discussion of FIG. 9.

Figure 13:
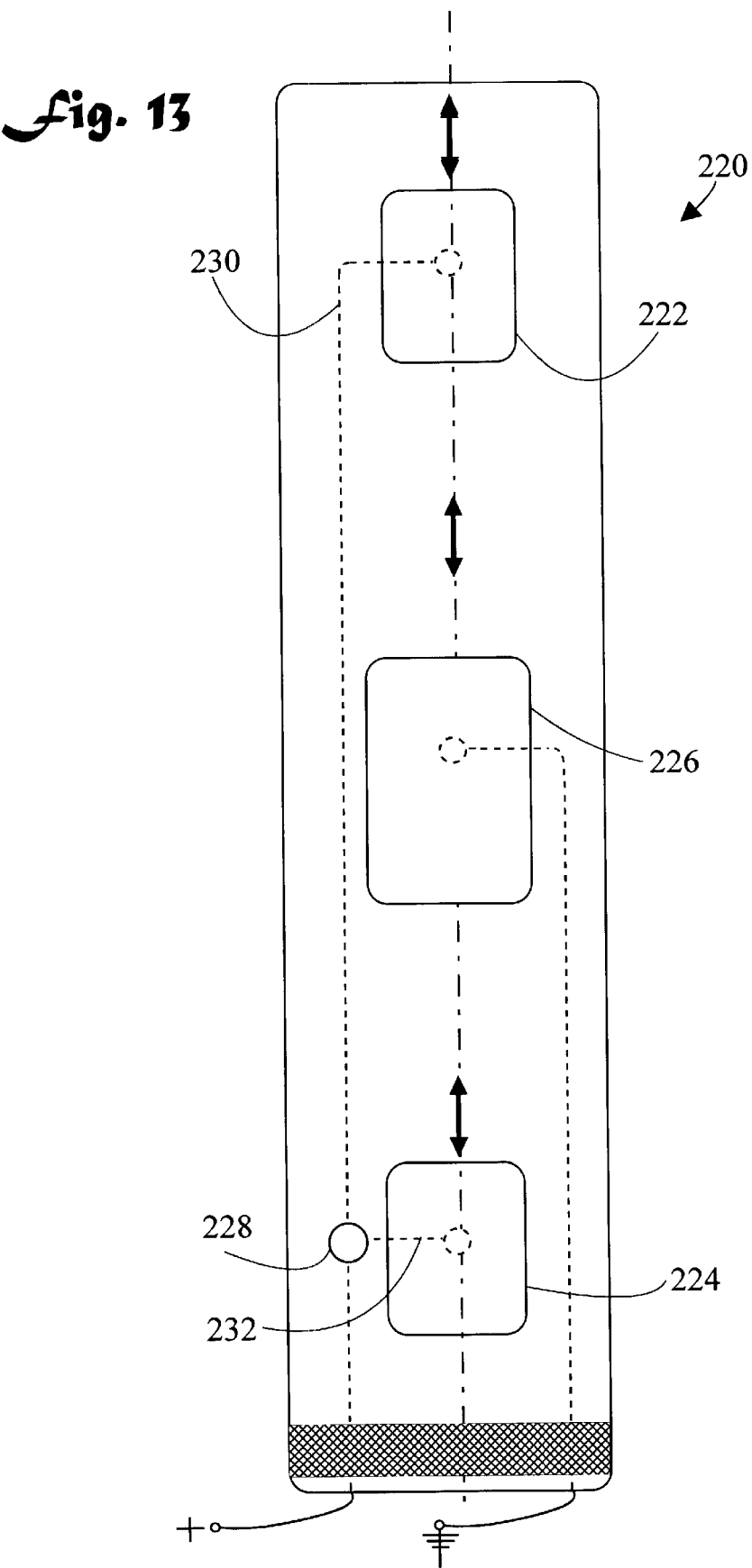
FIG. 13 is a top plan view of a third extremity cuff embodiment having both poles.
Figure 14:
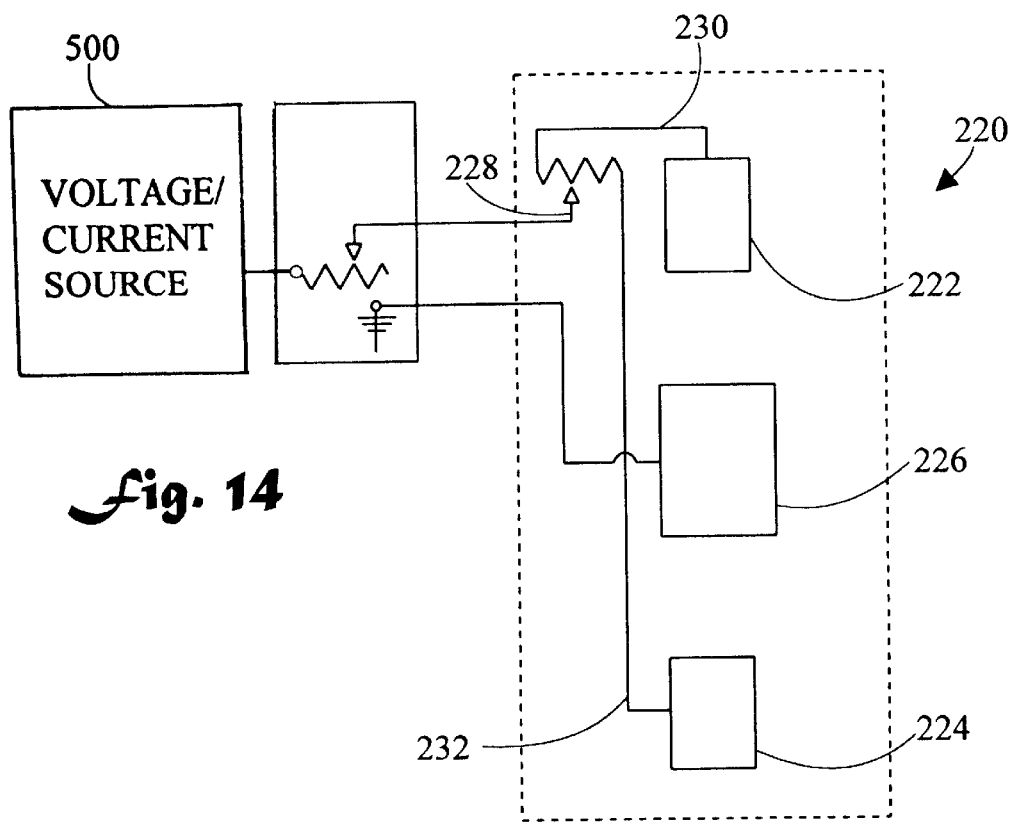
FIG. 14 is a schematic diagram of the third extremity cuff embodiment.

FIG. 13 is a top plan view of a third extremity cuff embodiment, generally designated as 220, having both poles on one belt. FIG. 14 is a schematic diagram of the third extremity cuff embodiment 220. Third extremity cuff 220 includes a first positive electrode 222 and a second positive electrode 224. A return electrode 226 is disposed between first positive electrode 222 and second positive electrode 224. An adjustment control 228 simultaneously applies a first positive voltage 230 to first positive electrode 222 and a second positive voltage 232 to second positive electrode 224. As first positive voltage 230 increases, second positive voltage 232 decreases. And as first positive voltage 230 decreases, second positive voltage 232 increases. That is, adjustment control 228 functions much as the balance control on a stereo. A voltage/current source 500 applies an electrical stimulation signal input as shown and described in FIG. 4. Cuff 220 is designed for the application of traverse stimulation. In this application, a single cuff 220 is utilized in which the positive and return electrodes are placed on the same cuff. The central return electrode 226 is somewhat larger in surface area than the positive electrodes 222 and 224. This design allows the concentration of stimuli to the return electrode to become dispersed in order to dilute the intensity of the stimulation feed from both positive electrodes 222 and 224. It may be readily appreciated that the positive and return negative or ground electrodes may be reversed. It may be appreciated that the selectively positionable electrode feature of embodiment 20 may also apply to embodiment 220.

When the extremity cuff 20 of FIGS. 1, 4, 10, and 11 is used, a patient 506 selects muscles to receive EMS. Extremity cuff device 20 is placed on the patient 506 so that electrodes 22 are adjacent to the selected muscles. To accomplish this, electrodes 22 may be selectively positioned on the flexible covering or band 24. A stimulation signal input 502 is provided by a voltage source 500 such as an EMS machine, which has its own output control, to a master adjustment control 504 located either directly on the belt or in a remote box, then to each individual adjustment control 32, and then to the electrodes 22. The master adjustment control 504 and the individual adjustment controls 32 are then adjusted to produce the desired level of stimulation to the selected muscles. The individual adjustment controls 32 are "tuned" so that one muscle receives the highest level of stimulation, and another muscle receives a lower level of stimulation. Throughout the stimulation process, the patient 506 can provide information as to the perceived level of stimulation as the master adjustment control 504 and individual adjustment controls 32 are adjusted.

In one preferred treatment method, the master adjustment control 504 is initially adjusted to a mid-level level position, e.g. 1.5 volts. After a period of time, the master adjustment control 504 is increased to a higher level, e.g. 3 volts. After another period of time, the master adjustment control 504 is decreased, e.g. to 1.5 volts. This procedure allows the patient 506 to start off with light exercise, move to more vigorous exercise, and then to lighter exercise as the patient 506 becomes tired. The electrical stimulation level also needs to be lessened as perspiration increases the conductivity of the stimulation signal to the muscles.

When two extremity cuff embodiments 20 are used, the electrodes 22 of the second flexible covering or band 24 receive a return signal 38 rather than a positive stimulation signal 34. The two extremity cuff embodiments 20 are selectively spaced apart on an extremity of the patient 506 as shown in FIG. 11 and provide longitudinal stimulation along the leg rather than the transectional stimulation provided by a single cuff as shown in FIG. 10.

Figure 15:
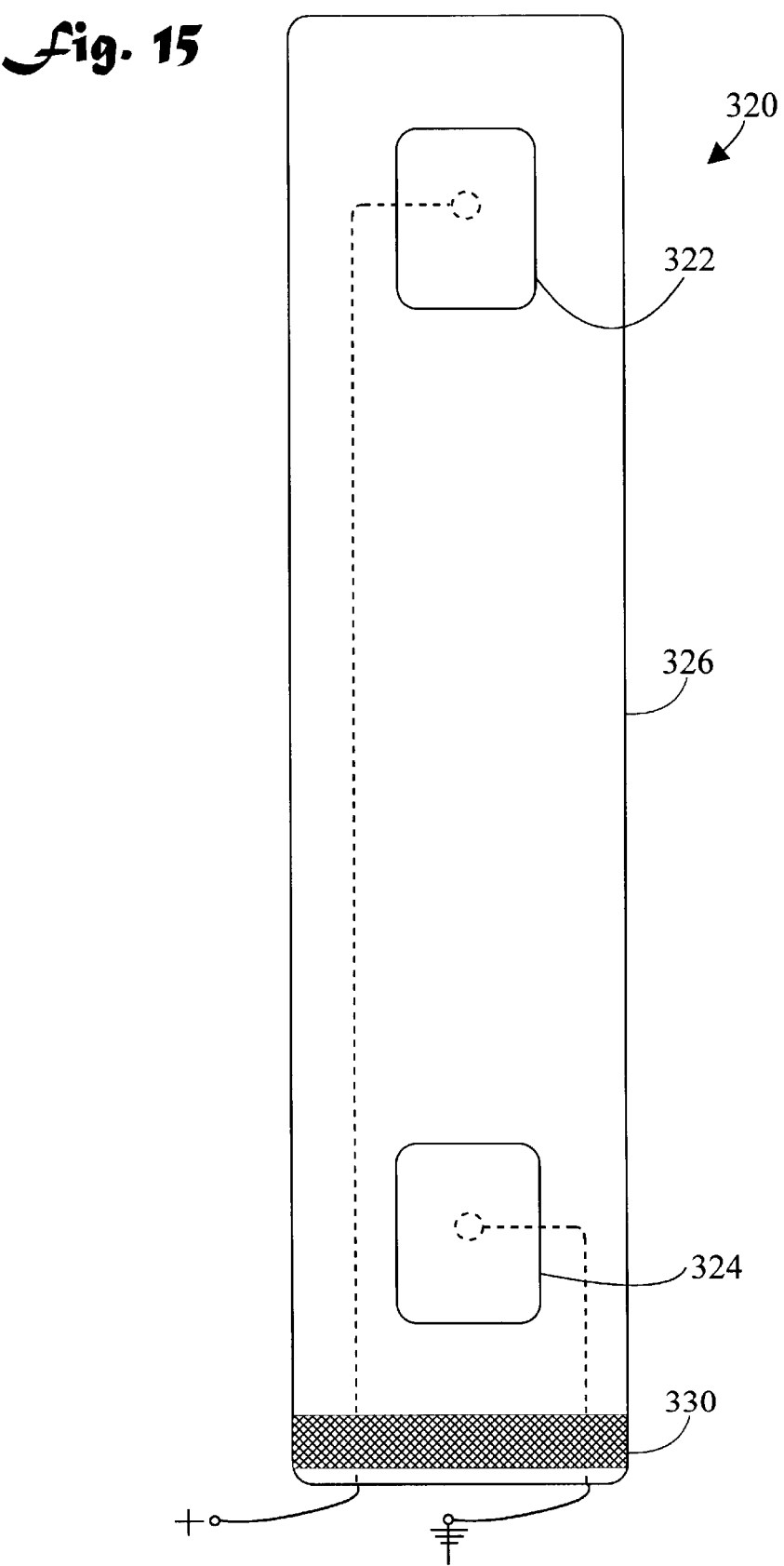
FIG. 15 is a top plan view of a fourth extremity cuff embodiment having both poles.

FIG. 15 illustrates a top plan view of a fourth extremity cuff embodiment, generally designated 320, having only two electrodes. Extremity cuff 320 includes a first positive electrode 322, a second return electrode 324, a connector 330, and flexible covering 326. It may be appreciated that the selectively positionable electrode and the individual adjustment control features of embodiment 20 may also apply to embodiment 120.

Figure 16:
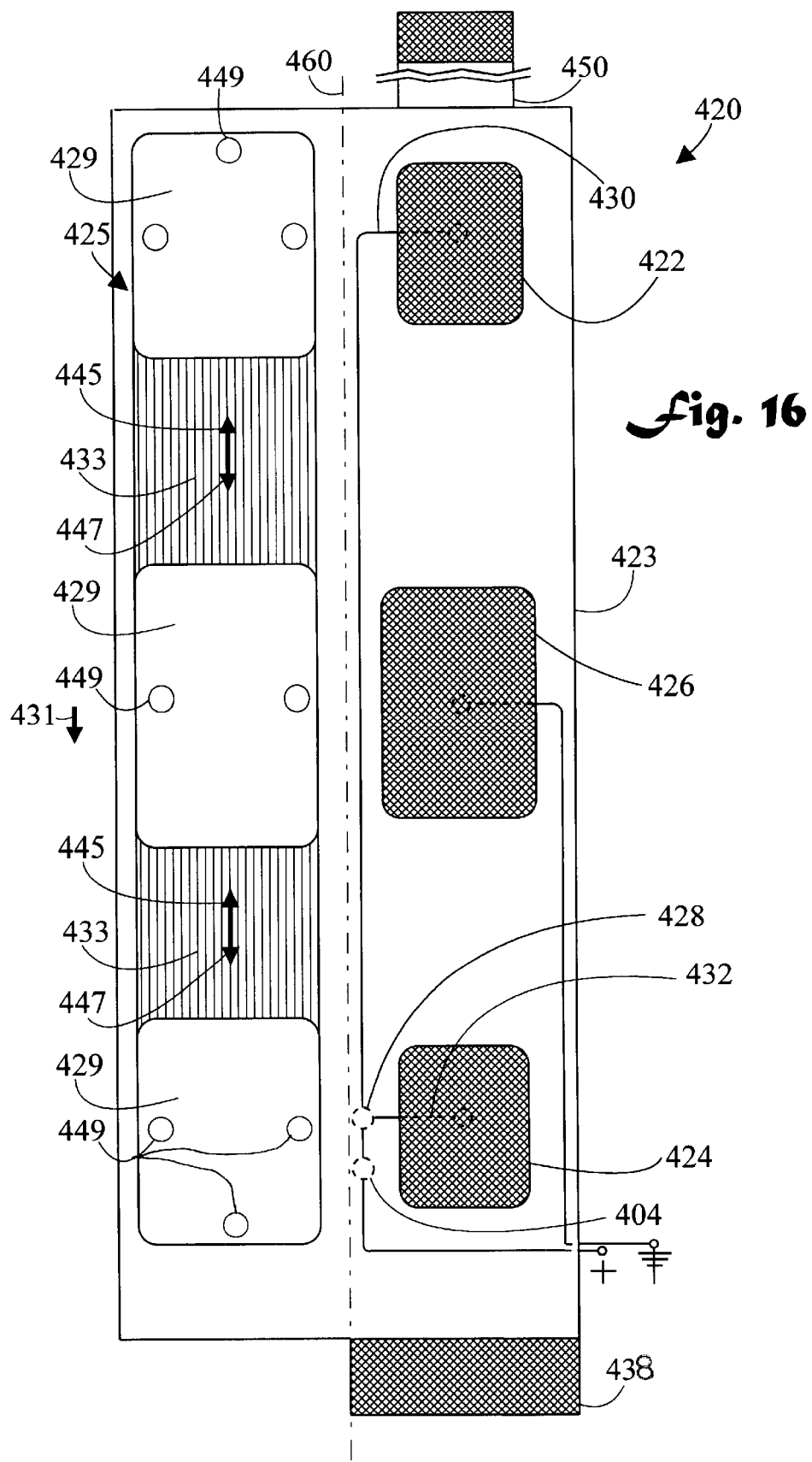
FIG. 16 is a top plan view of the fifth extremity cuff embodiment in an unfolded open configuration.

FIG. 16 illustrates a top plan view of a fifth extremity cuff embodiment in its unfolded open configuration, generally designated as 420. Extremity cuff 420 includes flexible covering 423, a plurality of longitudinally spaced electrodes 422, 424, and 426, and a sponge assembly 425 having a plurality of longitudinally spaced electrode abutting sponges

429. Sponge assembly 425 is selectively removable from extremity cuff 420 by sliding it in direction 431. As shown in FIGS. 18 and 19, flexible covering 423 is folded over and fashioned in the form of an elongated pocket into which sponge assembly 425 may be selectively slidably inserted and removed.

Since sponges 429 conduct electricity when they are damp, sponges 429 are connected by a nonconducting web 433. In a preferred embodiment, nonconducting web 433 is stretchable in directions 445 and 447, as is flexible covering 423. Also, sponges 429 are selectively removable from sponge assembly 425. When the sponges 429 become contaminated with dirt and sweat, they can be replaced. The removal process is effected with snaps 449.

Electrodes 422 and 424 are connected to a positive voltage, while electrode 426 is connected to the return. The connection is effected by a socket (not shown) located on flexible covering 423. In a preferred embodiment, fifth extremity cuff embodiment 420 includes the same balance adjustment feature that was previously described for third cuff embodiment 220 shown in FIGS. 13 and 14. An adjustment control 428 (see also FIG. 20) simultaneously applies a first positive voltage 430 to first positive electrode 422 and a second positive voltage 432 to second positive electrode 424. As first positive voltage 430 increases, second positive voltage 432 decreases. And as first positive voltage 430 decreases, second positive voltage 432 increases. A master adjustment control 404 is also located on fourth extremity cuff embodiment 420 to control the overall voltage level. Electrodes 422, 424, and 426 are fabricated from a wire mesh. Latex is used to coat the edges of the wire mesh to prevent snagging. In a preferred embodiment, flexible covering 423 is fabricated from neoprene. A belt 450 having a connector (also refer to FIG. 21) is attached to flexible covering 423 and is utilized to hold flexible covering 423 tightly around the user. Flexible covering 423 has a flap 438 having connector material used to close the elongated pocket of the fifth extremity cuff embodiment and to provide access to sponge assembly 425.

Figure 17:
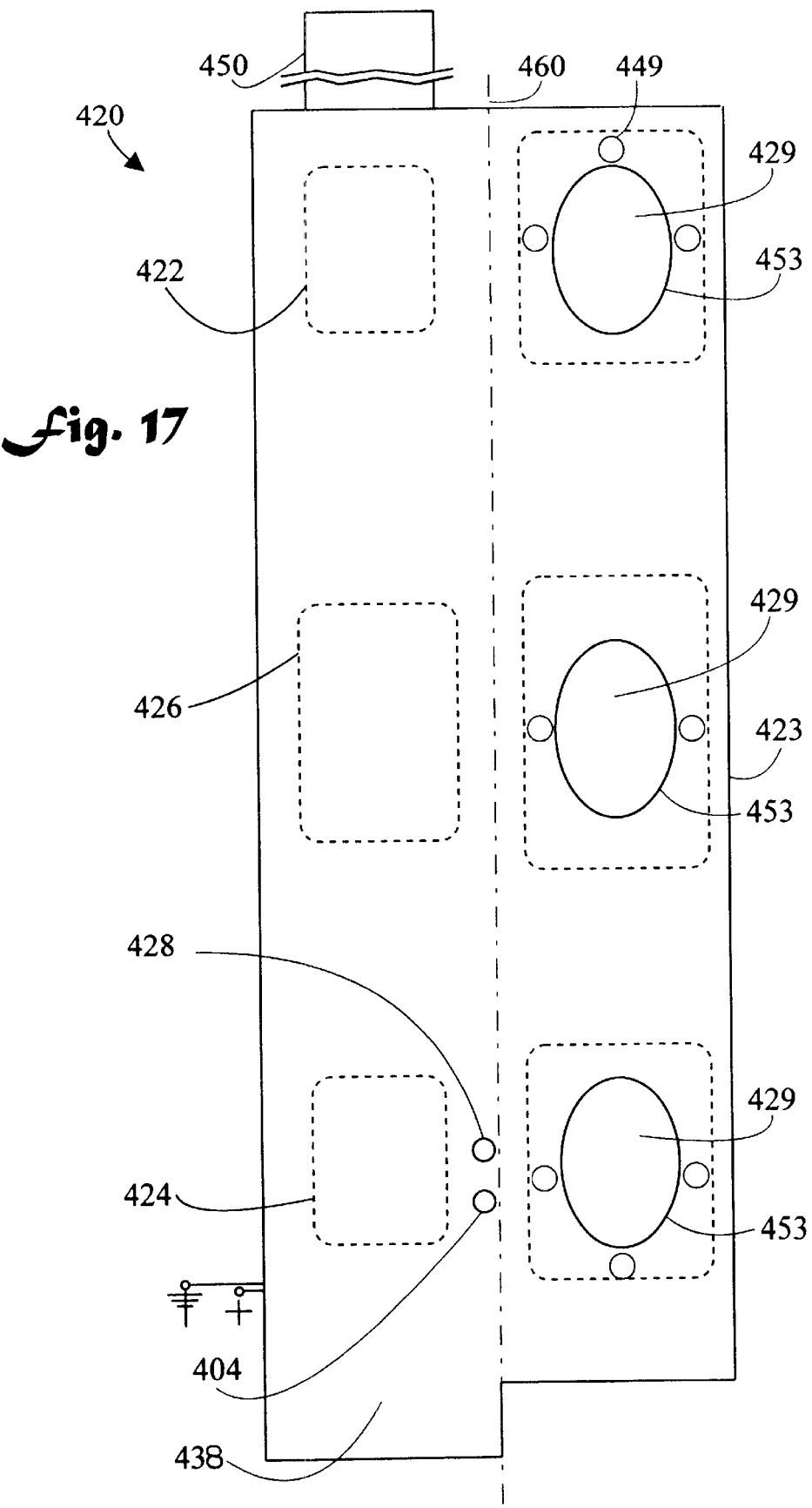
FIG. 17 is a bottom plan view of the fifth extremity cuff embodiment.

FIG. 17 is a bottom plan view of fifth extremity cuff embodiment 420. Holes 453 are cut in flexible covering 423 directly over sponges 429 so that sponges 429 may come into contact with the user's skin. The snaps 449 hold the edges of the sponges 429 to keep them from passing through the holes 453.

FIG. 18 is a top plan view of fifth extremity cuff embodiment 420 in the folded and ready for use configuration. From FIG. 16, the left side has been folded under the right side in direction 458 generally along axis 460. Stretchable zigzag stitching 465 is used to form flexible covering 423 into an elongated pocket into which sponge assembly 425 can slidably fit. Flap 438 has been folded over in direction 470 to close the open end of the pocket.

FIG. 19 is a cross sectional view along the line 19—19 of FIG. 18 showing the folded and sewn flexible covering 423.

Figure 20:
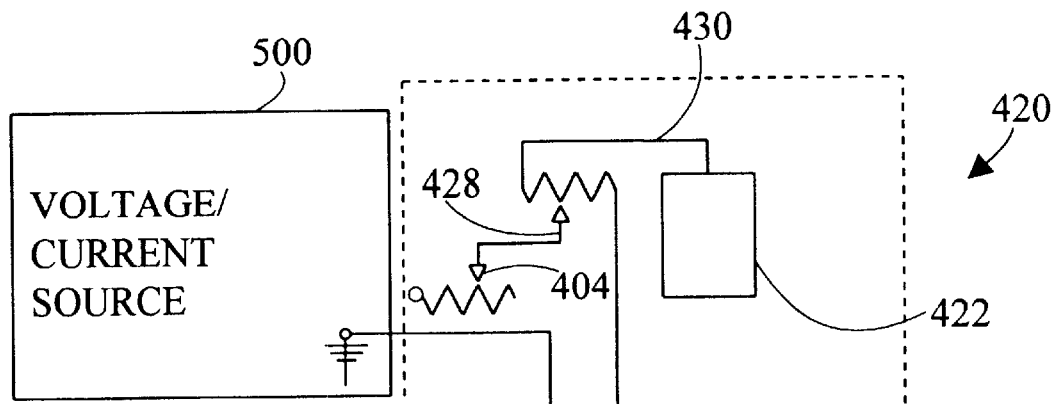
FIG. 20 is a schematic diagram of the fifth extremity cuff embodiment.

FIG. 20 is a schematic diagram of fifth extremity embodiment 420. Master adjustment control 404 and balance adjustment control 428 are both mounted on the flexible covering.

Figure 21:
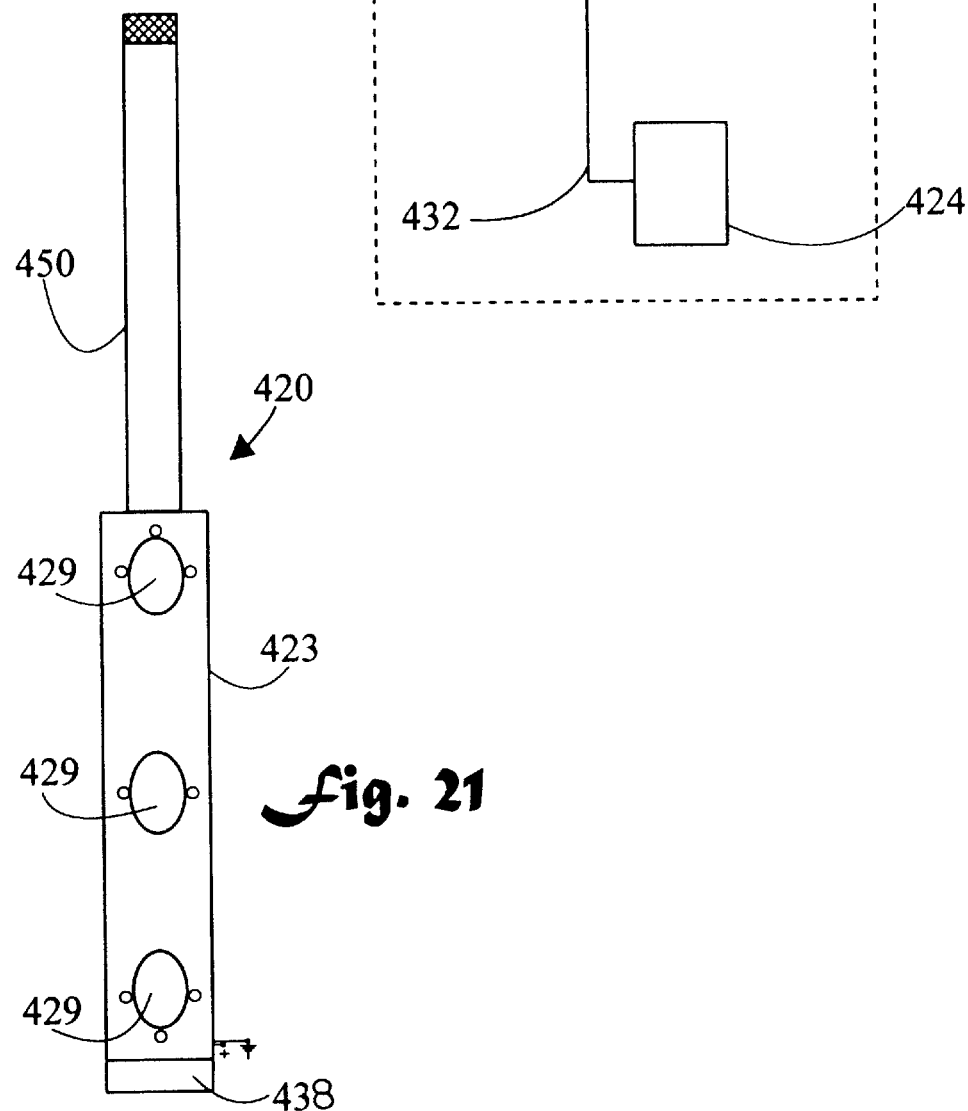
FIG. 21 is a reduced top plan view of the fifth extremity cuff embodiment.

FIG. 21 is a reduced top plan view of the fifth extremity cuff embodiment 420. Belt 450 loops up and over the top of the sponges 429 and attaches to the other end of the cuff at flap 438.

The preferred embodiments of the invention described herein are exemplary and numerous modifications, dimensional variations, and rearrangements can be readily envisioned to achieve an equivalent result, all of which are intended to be embraced within the scope of the appended claims.

I claim:

1. A device for administrating electro-muscle stimulation, comprising a flexible covering having a plurality of spaced apart electrodes, said electrodes disposed in a pattern upon said flexible covering which matches a predetermined group of human muscles, so that when said flexible covering is placed upon a patient, said electrodes are proximate to the predetermined group of muscles, wherein said pattern matches predetermined groups of muscles, the muscles being the upper portion of the rectus abdominus, the lower portion of the rectus abdominus, the right obliques, and the left obliques.

2. A device according to claim 1,
said electrodes including:
a first positive said electrode for placement proximate to the upper portion of the rectus abdominus;
a second positive said electrode for placement proximate to the lower portion of the rectus abdominus,
a third return said electrode disposed between said first positive and second positive electrodes; and,
a voltage source connected between said positive electrodes and said return electrode.

3. A device according to claim 2,
said electrodes including:
a fourth positive said electrode for placement on the right obliques on the side of the abdomen above the iliac crest;
a fifth return said electrode for placement proximate to the junction of the right obliques and the upper and lower portions of the rectus abdominus;
said fifth return said electrode disposed between said fourth positive said electrode and said third return said electrode; and,
a voltage source connected between said positive electrode and said return electrodes.

4. A device according to claim 2,
said electrodes including:
a sixth positive said electrode for placement on the left obliques on the side of the abdomen above the iliac crest;
a seventh return said electrode for placement proximate to the junction of the left obliques and the upper and lower portions of the rectus abdominus;
said seventh return said electrode disposed between said sixth positive said electrode and said third return said electrode; and,
a voltage source connected between said positive electrode and said return electrodes.

5. A device according to claim 2, said second positive said electrode shaped so as to avoid stimulation of the femoral nerve.

6. A device according to claim 1, further including:
said flexible covering having the general shape of a band having two ends;
a connector for connecting said two ends.

7. A device according to claim 1, further including:
an individual adjustment control for each said electrode individually controlling the stimulus to the upper portion of the rectus abdominus, the lower portion of the rectus abdominus, the right obliques, and the left obliques; and,
a master amplitude adjustment control connected to all said electrodes.

8. A device for administrating electro-muscle stimulation, comprising:
- a flexible covering having a plurality of spaced apart electrodes;
- said electrodes including:
  - a first positive electrode;
  - a second positive electrode;
  - a return electrode disposed between said first and second positive electrodes;
- a voltage source connected between said positive electrodes and said return electrode; and,
- an adjustment control which simultaneously applies a first positive voltage to said first positive electrode and a second positive voltage to said second positive electrode, so that as said first positive voltage increases, said second positive voltage decreases, and as said first positive voltage decreases, said second positive voltage increases.

9. A device for administrating electro-muscle stimulation, comprising:
- a flexible covering having a plurality of spaced apart electrodes;
- a sponge assembly having a corresponding plurality of longitudinally spaced sponges which abut said plurality of electrodes; and,
- said plurality of sponges connected by a stretchable nonconducting web.

10. A device for administrating electro-muscle stimulation, comprising:
- a flexible covering having a plurality of spaced apart electrodes;
- a sponge assembly having a corresponding plurality of longitudinally spaced sponges which abut said plurality of electrodes; and,
- said flexible covering fashioned in the form of an elongated pocket; and,
- said sponge assembly selectively slidable into said pocket.

11. A device according to claim 10, said pocket formed by stretchable zigzag stitching.

* * * * *